(12) United States Patent
Zhang et al.

(10) Patent No.: US 9,198,632 B2
(45) Date of Patent: Dec. 1, 2015

(54) METHOD FOR SCATTERING CORRECTION FOR SPARSELY DISTRIBUTED STATIONARY DETECTORS AND ROTATING X-RAY SOURCE

(71) Applicants: Kabushiki Kaisha Toshiba, Minato-ku (JP); Toshiba Medical Systems Corporation, Otawara-shi (JP)

(72) Inventors: Yuexing Zhang, Naperville, IL (US); Yu Zou, Naperville, IL (US); Daniel Gagnon, Twinburg, OH (US)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 266 days.

(21) Appl. No.: 13/780,900

(22) Filed: Feb. 28, 2013

(65) Prior Publication Data

US 2014/0241489 A1     Aug. 28, 2014

(51) Int. Cl.
*G21K 1/10*  (2006.01)
*A61B 6/00*  (2006.01)
*A61B 6/03*  (2006.01)

(52) U.S. Cl.
CPC .............. *A61B 6/5282* (2013.01); *A61B 6/032* (2013.01); *A61B 6/4241* (2013.01); *A61B 6/4275* (2013.01); *A61B 6/482* (2013.01)

(58) Field of Classification Search
CPC .... A61B 6/5282; A61B 6/032; A61B 6/4241; A61B 6/4275; A61B 6/482; A61B 6/03; A61B 6/483; A61B 3/102; A61B 6/00; A61B 8/00; A61B 15/005; A61B 15/06; A61B 15/08; A61B 15/40; A61B 15/60; G21K 1/10; G06T 11/005; G06T 2207/10116; G06T 5/003; G06T 15/005; G06T 15/06; G06T 15/08; G06T 15/40; G06T 15/60; G06T 2207/10101; G06T 2207/20116
USPC ............................................. 378/4, 7, 9, 15, 62
See application file for complete search history.

(56) References Cited

U.S. PATENT DOCUMENTS

| | | | |
|---|---|---|---|
| 7,697,658 B2 * | 4/2010 | Wang et al. ......................... 378/4 |
| 8,121,245 B2 * | 2/2012 | Pan et al. ............................ 378/2 |
| 8,280,135 B2 * | 10/2012 | McCollough et al. ......... 382/128 |
| 8,326,011 B2 * | 12/2012 | Star-Lack et al. .............. 382/131 |
| 8,798,350 B2 | 8/2014 | Zou | |
| 2009/0225932 A1 * | 9/2009 | Zhu et al. ........................... 378/7 |

FOREIGN PATENT DOCUMENTS

JP      2013-192951      9/2013

* cited by examiner

*Primary Examiner* — Irakli Kiknadze
(74) *Attorney, Agent, or Firm* — Oblon, McClelland, Maier & Neustadt, L.L.P.

(57) ABSTRACT

A spectral computed tomography scanner apparatus, including a rotating X-ray source, a plurality of fixed energy-discriminating detectors, a processor that generates a shadow map that indicates, for each detector/view angle, a shadow state of the detector, the shadow state indicating that one of X-rays are completely blocked by a second detector and do not reach the detector, the X-rays are partially blocked by the second detector and partially reach the detector, the X-rays are not blocked by any of the detectors and reach the detector, and the detector is not with the scan field of view at the view angle, and a controller configured to cause the scanner apparatus to perform a scan of an object over a first range of view angles to collect view data, wherein the processor is configured to perform scatter correction using the collected view data and the generated shadow map.

14 Claims, 5 Drawing Sheets

METHOD FOR SCATTERING CORRECTION FOR SPARSELY DISTRIBUTED STATIONARY DETECTORS AND ROTATING X-RAY SOURCE

FIELD

Embodiments disclosed herein generally relate to computed tomography (CT) imaging. In particular, embodiments disclosed herein relate to a system and an associated method to perform scattering correction for sparsely distributed stationary detectors with a rotating X-ray source so as to support an overall more accurate image reconstruction.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed. In the reconstruction, the map of the linear attenuation coefficient (LAC) of the imaged subjects is obtained from the line integrals of the LAC through an inverse Radon transform. The line integrals can be related to the logarithm of the primary intensity of the X-rays passing through the subject. However, the measured X-ray intensity on the detector may include both scattering photons and primary photons. Thus, the images reconstructed from scattering, contaminated intensities may contain some scattering artifacts.

A third generation CT system can include sparsely distributed fourth generation, photon-counting detectors. In such a combined system, the fourth generation detectors collect primary beams through a range of detector fan angles, preventing the use of anti-scatter grids. Thus, for such a combined third/fourth generation system, scattering is a significant problem. In particular, for multi-slice CT, especially wide-cone CT, the scattered X-ray intensity can be equal to or higher than the intensity of the primary beam. Further, for spectral CT, the scattered X-ray intensity affects not only the detected count rate, but also the spectral measurement.

Conventionally, several schemes have been proposed for reducing scattering in third generation CT. However, none of these schemes is appropriate for sparsely distributed, fourth generation CT detectors.

For example, one conventional approach for third generation systems is the use of post-patient collimators to physically block scattering from reaching the detectors. However, this approach does not work for stationary, sparsely distributed fourth generation detectors, which need to receive X-ray beams for a large range of fan angles.

Further, conventional single-slice, fourth generation CT platforms have used a second row of detectors placed next to a first detector row for imaging in which signals from the second row are used to evaluate the scattering for the first detector row. However, this method does not work well when multiple rows of detectors are used for multi-slice CT.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
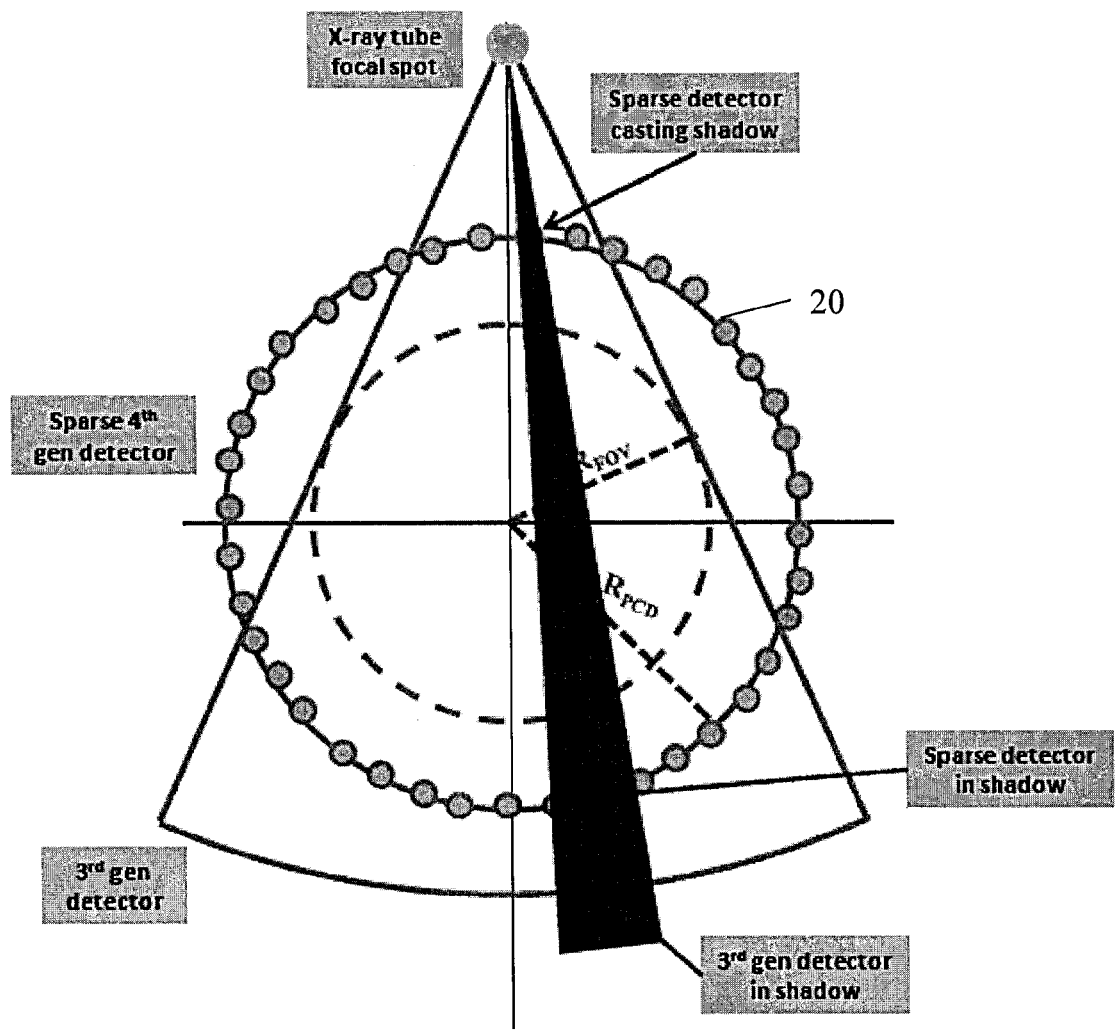
FIG. 1 illustrates a CT scanner apparatus including fixed photon-counting detectors, a rotating X-ray source, and third-generation detectors.

Embodiments described herein are directed to a new system and method for scattering correction for stationary, sparsely distributed fourth generation CT detectors.

In particular, in one embodiment there is provided a scatter-correction method for a spectral computed tomography (CT) scanner having a rotating X-ray source and a plurality of fixed energy-discriminating detectors, the method comprising: (1) generating a shadow map, the shadow map indicating, for each detector and for each view angle of the X-ray source, a shadow state of the detector, the shadow state indicating that one of (a) X-rays from the X-ray source are completely blocked by a second energy-discriminating detector and do not reach the detector, (b) the X-rays are partially blocked by the second detector and partially reach the detector, (c) the X-rays are not blocked at all by any of the detectors and reach the detector, and (d) the detector is not with the scan field of view (SFOV) of the X-ray source at the view angle; (2) performing a scan of an object using the CT scanner over a first range of view angles to collect view data; and (3) performing scatter correction using the collected view data and the generated shadow map.

In one embodiment, the generating step comprises pre-calculating the shadow map for each view angle from known positions of the detectors.

In another embodiment, the generating step comprises: (1) performing, with the CT scanner, an air scan for a predetermined range of view angles to obtain air scan data for each detector at each view angle of the predetermined range of view angles; and (2) generating the shadow map by determining, using the obtained air scan data, the shadow state of each detector at each view angle of the predetermined range of view angles.

In another embodiment, the CT scanner further includes a plurality of non-energy-discriminating detectors, and the step of generating the shadow map comprises: (1) performing, with the CT scanner, a first air scan without the energy-discriminating detectors for a predetermined range of view angles to obtain first air scan data for each non-energy-discriminating detector at each view angle of the predetermined range of view angles; (2) performing, with the CT scanner, a second air scan with the energy-discriminating detectors for the predetermined range of view angles to obtain second air scan data for each non-energy-discriminating detector and each energy-discriminating detector at each view angle of the predetermined range of view angles; and (3) generating the shadow map by determining, using the obtained first and second air scan data, the shadow state of each non-energy-discriminating detector and each energy-discriminating detector at each view angle of the predetermined range of view angles.

In yet another embodiment, the generating step comprises determining, for a given detector at a given view angle, whether the detector is completely blocked, partially blocked, or not blocked by comparing the first air scan data and the second air scan data for the given detector at the given view angle.

In one embodiment, the scatter correction step comprises (1) reading an entry in the shadow map for a given detector at a given view angle; (2) when the entry read from the shadow map indicates that the given detector at the given view angle was completely blocked, determining that the corresponding view data for the given detector at the given view angle represents a scatter signal; and (3) performing scatter correction for detectors that are adjacent to the given detector in space or time using the determined scatter signal.

In another embodiment, the scatter correction step comprises: (1) reading an entry in the shadow map for a given detector at a given view angle; (2) when the entry read from the shadow map indicates that the given detector at the given view angle was partially blocked, determining a scatter signal and a primary signal for the given detector using the collected view data at the given detector and the collected view data at at least one detector that is adjacent to the given detector in space or time; and (3) performing scatter correction for detectors that are adjacent to the given detector in space or time using the determined scatter signal.

According to another embodiment there is provided a spectral computed tomography (CT) scanner apparatus, comprising: (1) a rotating X-ray source; (2) a plurality of fixed energy-discriminating detectors; (3) a processor configured to generate a shadow map, the shadow map indicating, for each detector and for each view angle of the X-ray source, a shadow state of the detector, the shadow state indicating that one of (a) X-rays from the X-ray source are completely blocked by a second energy-discriminating detector and do not reach the detector, (b) the X-rays are partially blocked by the second detector and partially reach the detector, (c) the X-rays are not blocked at all by any of the detectors and reach the detector, and (d) the detector is not with the scan field of view (SFOV) of the X-ray source at the view angle; (4) a controller configured to cause the scanner apparatus to perform a scan of an object over a first range of view angles to collect view data, wherein the processor is configured to perform scatter correction using the collected view data and the generated shadow map.

In one embodiment, in generating the shadow map, the processor is further configured to pre-calculate the shadow map for each view angle from known positions of the detectors.

In one embodiment, in generating the shadow map, the processor is further configured to: (1) cause the controller to control the scanner apparatus to perform an air scan for a predetermined range of view angles to obtain air scan data for each detector at each view angle of the predetermined range of view angles; and (2) generate the shadow map by determining, using the obtained air scan data, the shadow state of each detector at each view angle of the predetermined range of view angles.

In one embodiment, the apparatus further comprises a plurality of non-energy-discriminating detectors, wherein, in generating the shadow map, the processor is further configured to: (1) cause the controller to control the scanner apparatus to perform a first air scan without the energy-discriminating detectors for a predetermined range of view angles to obtain first air scan data for each non-energy-discriminating detector at each view angle of the predetermined range of view angles; (2) cause the controller to control the scanner apparatus to perform a second air scan with the energy-discriminating detectors for the predetermined range of view angles to obtain second air scan data for each non-energy-discriminating detector and each energy-discriminating detector at each view angle of the predetermined range of view angles; and (3) generate the shadow map by determining, using the obtained first and second air scan data, the shadow state of each non-energy-discriminating detector and each energy-discriminating detector at each view angle of the predetermined range of view angles.

In one embodiment, in generating the shadow map, the processor is further configured to determine, for a given detector at a given view angle, whether the detector is completely blocked, partially blocked, or not blocked by comparing the first air scan data and the second air scan data for the given detector at the given view angle.

In one embodiment, in performing the scatter correction, the processor is further configured to: (1) read an entry in the shadow map for a given detector at a given view angle; (2) when the entry read from the shadow map indicates that the given detector at the given view angle was completely blocked, determine that the corresponding view data for the given detector at the given view angle represents a scatter signal; and (3) perform scatter correction for detectors that are adjacent to the given detector in space or time using the determined scatter signal.

In one embodiment, in performing the scatter correction, the processor is further configured to: (1) read an entry in the shadow map for a given detector at a given view angle; (2) when the entry read from the shadow map indicates that the given detector at the given view angle was partially blocked, determine a scatter signal and a primary signal for the given detector using the collected view data at the given detector and the collected view data at at least one detector that is adjacent to the given detector in space or time; and (3) perform scatter correction for detectors that are adjacent to the given detector in space or time using the determined scatter signal.

Turning now to the drawings, FIG. 1 illustrates a combine third/fourth generation system having stationary, sparsely distributed fourth generation detectors, along with a rotating third generation source/detector system. As shown in FIG. 1, the sparse detectors cast shadows onto other sparse detectors. As explained in more detail below, the shadows on the sparse detectors are used to evaluate scatter.

Figure 2:
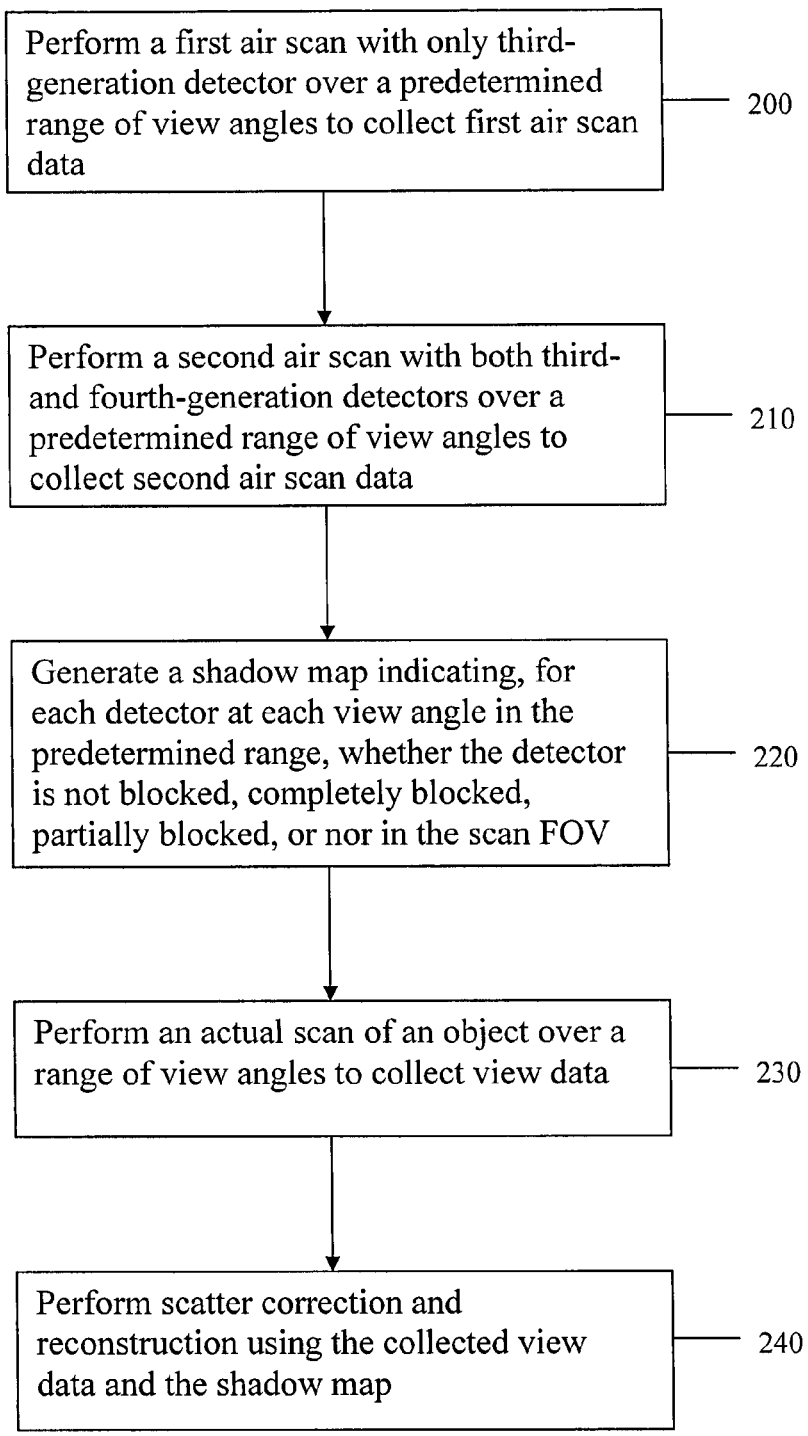
FIG. 2 illustrates a scatter-correction method of the present embodiments.

FIG. 2 illustrates a flowchart for a method of scatter correction in a combine $3^{rd}/4^{th}$ generation system according to one embodiment.

In step 200, an air scan is performed for the system of FIG. 1, but with the fourth generation photon-counting detectors removed. This initial air scan is performed for a full set of views and data is collected at each third-generation detector for each view.

In step 210, a second air scan is performed for the system of FIG. 1, including both the third- and fourth-generation detector elements. The second air scan is performed for the same set of views as performed in the initial air scan, and data is collected at each third-generation detector and at each fourth-generation detector for each view.

In step 220, a shadow map/table is generated based on the data collected in steps 200 and 210. The shadow map include a shadow data value for each detector element for each view. The shadow data generally indicates whether a particular detector element is in shadow for a particular view.

In particular, in one embodiment, the shadow value, for each view and each detector element, is one of the following four values: (1) "off," meaning that for the given view, the given detector element is not in the field of view; (2) "not blocked," meaning that X-rays from the source are not blocked at all by any of the fourth-generation detectors; (3) "completely blocked," meaning that all X-rays from the source are completely blocked by a fourth-generation detector; and (4) "partially blocked," meaning that X-rays from the source are partially blocked by a fourth-generation detector or that the given detector element is partially in shadow.

For example, for the third-generation detectors, data from the first air scan is compared with data from the second air scan to determine, for each view, which detector elements are not blocked, completely blocked, or partially blocked. For example, for a given view and detector, if the data value collected in the first air scan is I, and the data value collected in the second air scan is I/2, the given detector element would be classified as partially blocked in the shadow table. Similarly, if the data value collected in the second air scan is I, the given detector element would be classified as not blocked in the shadow table. Further, note that basic geometric calculations can be used to determine which detector elements are not in the field of view for a given view and detector. Moreover, geometric calculations can also be used in place of, or in combination with, the air scans described above to determine the values for the shadow map, for both the third- and fourth-generation detectors.

For the sparse, fourth-generation detectors, the view sampling frequency can be increased so that, for a given view, at least one detector is completely blocked so that the collected data represents the scatter signal.

In step 230, an actual scan of an object is performed over at least a subset of the views used for the air scans to generate a set of view data used for reconstruction.

In step 240, the shadow map is used in combination with the set of data collected in step 230 to perform scatter correction prior to reconstruction. In particular, for each view and each detector, the view data is processed based on the corresponding entry in the shadow map. After processing the collected view data based on the shadow map to obtain scatter signals, reconstruction is performed using the obtained scatter signals.

For example, for a given view/detector combination, if the shadow map indicates that the detector element was completely blocked, the collected view data is due only to scatter. Thus, with the assumption that scatter changes slowly both spatially and temporally, the collected view data can be used as the scatter signal for detector elements that are neighbors in either space or time, using conventional scatter-correction algorithms.

Further, for a given view/detector combination, if the shadow map indicates that the detector element was not blocked, no scatter information is available. In addition, for a given view/detector combination, if the shadow map indicates that the fourth-generation detector element was not in the FOV, the collected count data is due only to scatter, and is utilized for scatter correction using a specified scatter model. For example, the specified scatter model can have a number of adjustable parameters that are adjusted based on the measured counts outside the FOV.

When the shadow map indicates that, for a given view/detector combination, the detector was partially in shadow or that the primary beam was partially blocked by a PCD, the scatter signal can be calculated using a method for separating the primary signal from the scatter signal, as described below with respect to FIGS. 3 and 4.

Figure 3:
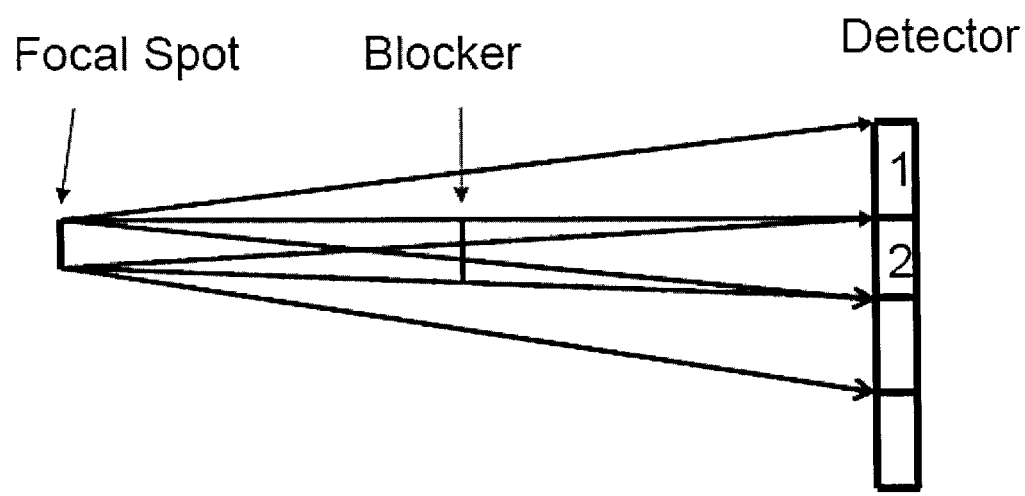
FIG. 3 illustrates scatter correction for adjacent elements that are partially blocked.
Figure 4:
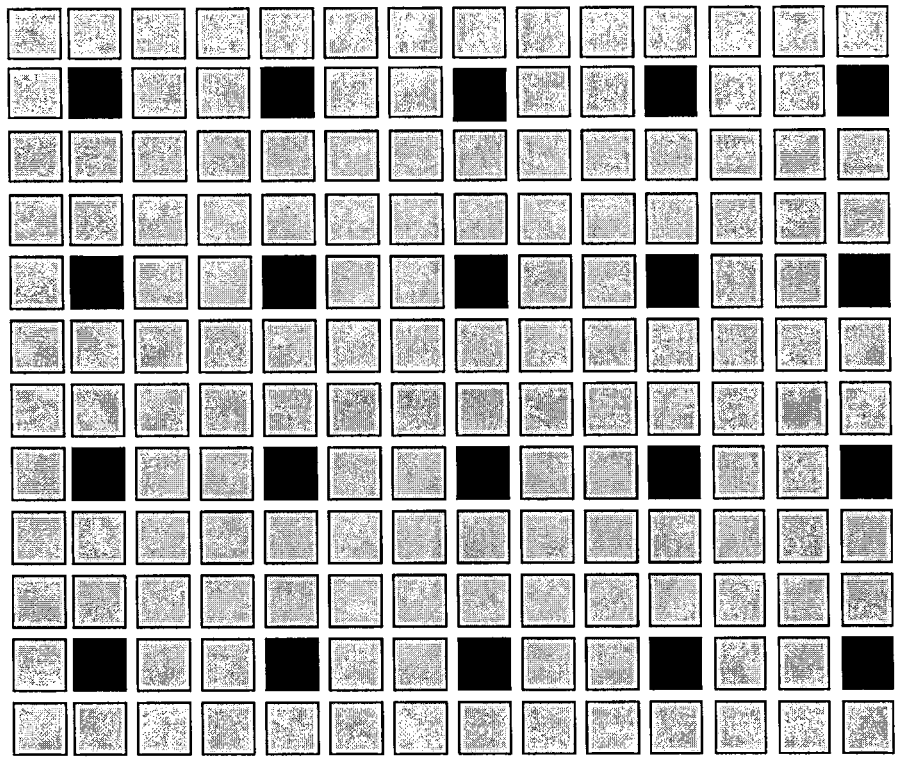
FIG. 4 illustrates scatter correction for adjacent elements in a two-dimensional array that are partially blocked.

FIG. 3 illustrates two neighboring detector elements and a blocking element that at least partially blocks the primary beam from reaching at least one of the detector elements.

The measured intensity at detector elements 1 and 2 for an actual scan of an object is given by $I(1)=I_0(1)e^{-g(1)}+I_s(1)$, and $I(2)=I_0(2)e^{-g(2)}+I_s(2)$, respectively, wherein $I_s(1)$ and $I_s(2)$ are the scatter signals at detector elements 1 and 2, and $I_0(1)$ and $I_0(2)$ are determined by an air scan. Here g is projection data or a line integral of linear attenuation coefficients (averaged over the spectrum). Then, assuming that $g(1) \approx g(2)$ and $I_s(1) \approx I_s(2)$, the two equations can be solved for the scatter signal at each detector element:

$$I_s(1) = I_s(2) = \frac{I_0(1)I(2) - I_0(2)I(1)}{I_0(1) - I_0(2)}.$$

Further, the primary signal is calculated as $$e^{-g} = \frac{I(1) - I(2)}{I_0(1) - I_0(2)}.$$

As is evident from these equations, if $I_0(1)=I_0(2)$, the equations can not be used to calculate the scatter and primary, since the denominator will be zero. However, when the measured air scan intensity values at neighboring elements differs due to, for example, partial blockage of the primary beam, the first equation above is used to estimate the scatter signal at each detector.

The above method is not limited to two neighboring detector elements, but can be performed on a general two- or three-dimensional geometry, including where one of the dimensions is time. For example, for the two-dimensional grid shown in FIG. 4, the black squares represent low incident intensity elements where the scatter signal is dominant. The other squares have normal intensities where the primary and scatter are mixed. Under the assumptions that the scatter intensity changes slowly and the line integral of the attenuation coefficients vary smoothly, the primary and scatter can be separated as follows.

For each block of nine neighboring detector elements (in a three-by-three block with a black square at the center), we have the measured actual scan intensity given by:

$$I(i)=I_0(i)e^{-g(i)}+I_s \text{ for } i=1, 2, \ldots 9.$$

Further, assuming that $$g(5) \approx \sum_{i=1 (i \neq 5)}^{9} w_i g(i),$$

we have 10 variables and ten equations, so that the system is closed and the scatter value $I_s$ can be calculated.

Note that, for the above-described method, since only sparse detector elements are used to measure the scatter signal, the spatial resolution of the reconstructed CT images is not degraded. Moreover, the above-described method allows for the reconstruction of scatter-free images such that an anti-scatter grid is unnecessary.

Further, the separated scatter signals can be used to reconstruct images of Rayleigh cross section (dark field imaging). Such images may have low spatial resolution, but are sensitive to the Rayleigh process. Conventional CT images are not sensitive to the Rayleigh process because the total Rayleigh cross section is much smaller than the total cross sections of photoelectric and Compton processes. Only the Compton and Rayleigh processes contribute to the scatter signals. Compton scattering is almost isotropic, while Rayleigh scattering is forward scatter. Rayleigh scattering and Compton scattering are comparable on the detector, although Compton scattering is dominant in the opposite direction.

Figure 5:
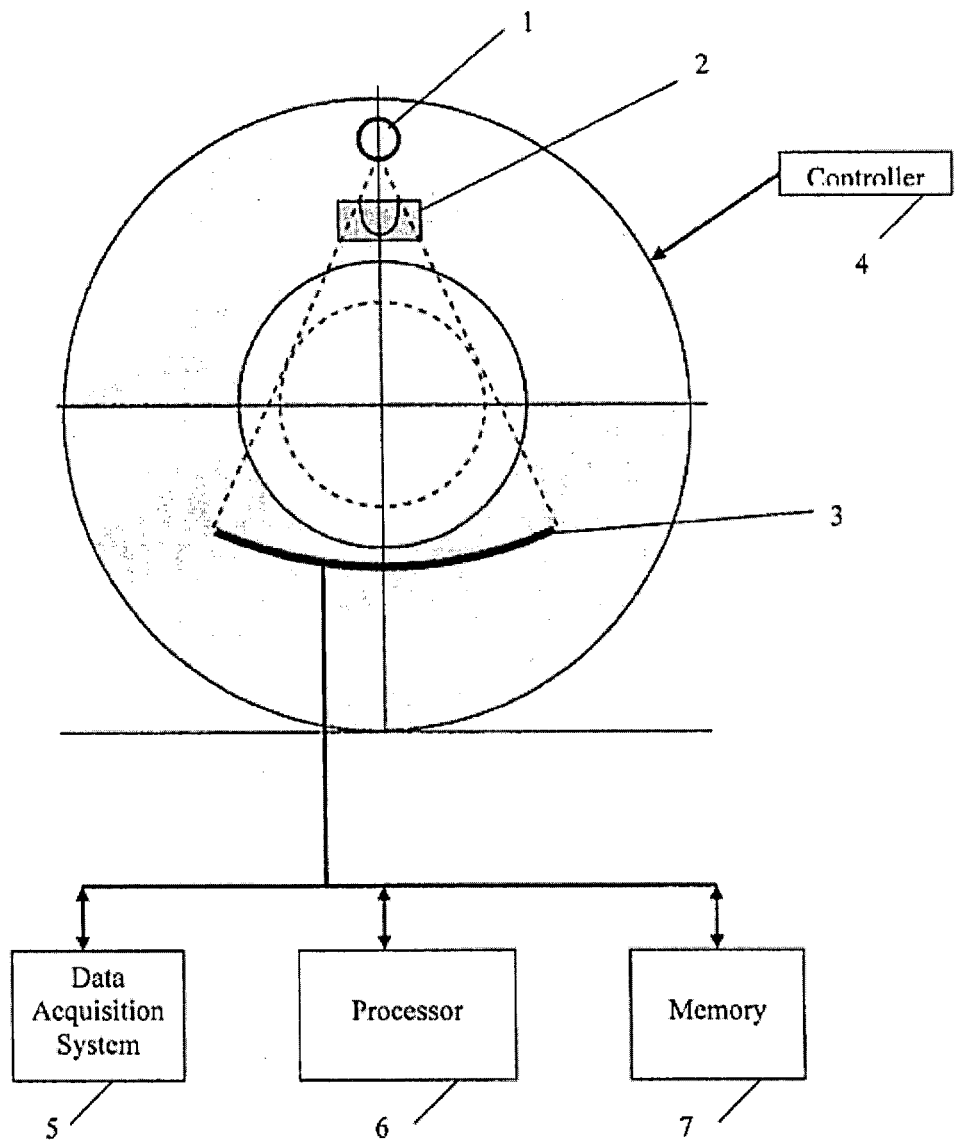
FIG. 5 illustrates a CT scanner system according to the present embodiments.

FIG. 5 illustrates the basic structure of a CT scanner apparatus that includes the detectors described herein. The CT apparatus of FIG. 5 includes an X-ray tube 1, filters and collimators 2, and detector 3. As shown in FIG. 1, the CT apparatus also includes sparse fixed energy-discriminating detectors. The CT apparatus will also include additional mechanical and electrical components such as a gantry motor and a controller 4 to control the rotation of the gantry, control the X-ray source, and control a patient bed. The CT apparatus also includes a data acquisition system 5 and a processor 6 to generate CT images based on the projection (view) data acquired by the data acquisition system. The processor makes use of a shadow map of the detectors that indicates which detector elements are completely blocked, partially blocked, not blocked, or not in the scan field of view, as described above. The processor and data acquisition system make use of a memory 7, which is configured to store, e.g., data obtained from the detector, the shadow map, and reconstructed images.

In one embodiment, the processor includes a pre-reconstruction processor configured to determine the total, primary, and scatter intensities using the scatter-correction algorithms discussed above. For example, in one embodiment, using the shadow map, the pre-reconstruction processor is configured to perform an algorithm to separate the scatter signal from the primary signal for detectors that are partially blocked.

In one embodiment, the spectral computed tomography (CT) scanner apparatus shown in FIGS. 1 and 5 includes a rotating X-ray source 1, a plurality of fixed energy-discriminating detectors 10; a processor 6 configured to generate a shadow map, the shadow map indicating, for each detector and for each view angle of the X-ray source, a shadow state of the detector, the shadow state indicating that one of (1) X-rays from the X-ray source are completely blocked by a second energy-discriminating detector and do not reach the detector, (2) the X-rays are partially blocked by the second detector and partially reach the detector, (3) the X-rays are not blocked at all by any of the detectors and reach the detector, and (4) the detector is not with the scan field of view (SFOV) of the X-ray source at the view angle; and a controller 6 configured to cause the scanner apparatus to perform a scan of an object over a first range of view angles to collect view data, wherein the processor is configured to perform scatter correction using the collected view data and the generated shadow map.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the pre-reconstruction processor, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A scatter-correction method for a spectral computed tomography (CT) scanner having a rotating X-ray source and a plurality of fixed energy-discriminating detectors, the method comprising:
   generating a shadow map, the shadow map indicating, for each detector and for each view angle of the X-ray source, a shadow state of the detector, the shadow state indicating that one of (1) X-rays from the X-ray source are completely blocked by a second energy-discriminating detector and do not reach the detector, (2) the X-rays are partially blocked by the second detector and partially reach the detector, (3) the X-rays are not blocked at all by any of the detectors and reach the detector, and (4) the detector is not with the scan field of view of the X-ray source at the view angle;
   performing a scan of an object using the CT scanner over a first range of view angles to collect view data; and
   performing scatter correction using the collected view data and the generated shadow map.

2. The method of claim 1, wherein the generating step comprises pre-calculating the shadow map for each view angle from known positions of the detectors.

3. The method of claim 1, wherein the generating step comprises:
   performing, with the CT scanner, an air scan for a predetermined range of view angles to obtain air scan data for each detector at each view angle of the predetermined range of view angles; and
   generating the shadow map by determining, using the obtained air scan data, the shadow state of each detector at each view angle of the predetermined range of view angles.

4. The method of claim 1, wherein the CT scanner further includes a plurality of non-energy-discriminating detectors, and the step of generating the shadow map comprises:

performing, with the CT scanner, a first air scan without the energy-discriminating detectors for a predetermined range of view angles to obtain first air scan data for each non-energy-discriminating detector at each view angle of the predetermined range of view angles;

performing, with the CT scanner, a second air scan with the energy-discriminating detectors for the predetermined range of view angles to obtain second air scan data for each non-energy-discriminating detector and each energy-discriminating detector at each view angle of the predetermined range of view angles; and generating the shadow map by determining, using the obtained first and second air scan data, the shadow state of each non-energy-discriminating detector and each energy-discriminating detector at each view angle of the predetermined range of view angles.

5. The method of claim 4, wherein the generating step comprises:

determining, for a given detector at a given view angle, whether the detector is completely blocked, partially blocked, or not blocked by comparing the first air scan data and the second air scan data for the given detector at the given view angle.

6. The method of claim 1, wherein the scatter correction step comprises:

reading an entry in the shadow map for a given detector at a given view angle;

when the entry read from the shadow map indicates that the given detector at the given view angle was completely blocked, determining that the corresponding view data for the given detector at the given view angle represents a scatter signal; and performing scatter correction for detectors that are adjacent to the given detector in space or time using the determined scatter signal.

7. The method of claim 1, wherein the scatter correction step comprises:

reading an entry in the shadow map for a given detector at a given view angle;

when the entry read from the shadow map indicates that the given detector at the given view angle was partially blocked, determining a scatter signal and a primary signal for the given detector using the collected view data at the given detector and the collected view data at at least one detector that is adjacent to the given detector in space or time; and performing scatter correction for detectors that are adjacent to the given detector in space or time using the determined scatter signal.

8. A spectral computed tomography (CT) scanner apparatus, comprising:

a rotating X-ray source;

a plurality of fixed energy-discriminating detectors;

a processor configured to generate a shadow map, the shadow map indicating, for each detector and for each view angle of the X-ray source, a shadow state of the detector, the shadow state indicating that one of (1) X-rays from the X-ray source are completely blocked by a second energy-discriminating detector and do not reach the detector, (2) the X-rays are partially blocked by the second detector and partially reach the detector, (3) the X-rays are not blocked at all by any of the detectors and reach the detector, and (4) the detector is not with the scan field of view of the X-ray source at the view angle; and a controller configured to cause the scanner apparatus to perform a scan of an object over a first range of view angles to collect view data, wherein the processor is configured to perform scatter correction using the collected view data and the generated shadow map.

9. The apparatus of claim 8, wherein, in generating the shadow map, the processor is further configured to pre-calculate the shadow map for each view angle from known positions of the detectors.

10. The apparatus of claim 8, wherein, in generating the shadow map, the processor is further configured to:

cause the controller to control the scanner apparatus to perform an air scan for a predetermined range of view angles to obtain air scan data for each detector at each view angle of the predetermined range of view angles; and generate the shadow map by determining, using the obtained air scan data, the shadow state of each detector at each view angle of the predetermined range of view angles.

11. The apparatus of claim 8, further comprising:

a plurality of non-energy-discriminating detectors, wherein, in generating the shadow map, the processor is further configured to:

cause the controller to control the scanner apparatus to perform a first air scan without the energy-discriminating detectors for a predetermined range of view angles to obtain first air scan data for each non-energy-discriminating detector at each view angle of the predetermined range of view angles;

cause the controller to control the scanner apparatus to perform a second air scan with the energy-discriminating detectors for the predetermined range of view angles to obtain second air scan data for each non-energy-discriminating detector and each energy-discriminating detector at each view angle of the predetermined range of view angles; and generate the shadow map by determining, using the obtained first and second air scan data, the shadow state of each non-energy-discriminating detector and each energy-discriminating detector at each view angle of the predetermined range of view angles.

12. The apparatus of claim 11, wherein, in generating the shadow map, the processor is further configured to:

determine, for a given detector at a given view angle, whether the detector is completely blocked, partially blocked, or not blocked by comparing the first air scan data and the second air scan data for the given detector at the given view angle.

13. The apparatus of claim 8, wherein, in performing the scatter correction, the processor is further configured to:

read an entry in the shadow map for a given detector at a given view angle;

when the entry read from the shadow map indicates that the given detector at the given view angle was completely blocked, determine that the corresponding view data for the given detector at the given view angle represents a scatter signal; and perform scatter correction for detectors that are adjacent to the given detector in space or time using the determined scatter signal.

14. The apparatus of claim 8, wherein, in performing the scatter correction, the processor is further configured to:

read an entry in the shadow map for a given detector at a given view angle;

when the entry read from the shadow map indicates that the given detector at the given view angle was partially blocked, determine a scatter signal and a primary signal for the given detector using the collected view data at the given detector and the collected view data at at least one detector that is adjacent to the given detector in space or time; and perform scatter correction for detectors that are adjacent to the given detector in space or time using the determined scatter signal.

* * * * *